United States Patent [19]
Sgro

[11] Patent Number: 6,059,735
[45] Date of Patent: May 9, 2000

[54] PORTABLE DEVICE FOR EXTEMPORANEOUS ANALYSIS OF A BODY-FLUID

[75] Inventor: Jean-Claude Sgro, Dijon, France

[73] Assignee: Bernard Chaffringeon, Saint-Suplice, Switzerland

[21] Appl. No.: 08/836,348

[22] PCT Filed: Nov. 20, 1995

[86] PCT No.: PCT/FR95/01527

§ 371 Date: Jul. 15, 1997

§ 102(e) Date: Jul. 15, 1997

[87] PCT Pub. No.: WO96/15725

PCT Pub. Date: May 30, 1996

[51] Int. Cl.[7] .................................................. A61B 10/00
[52] U.S. Cl. ............................................ 600/569; 600/573
[58] Field of Search ..................................... 600/573, 575, 600/576, 580, 581, 582, 583, 584, 562, 563, 569, 570, 572, 585, 339, 341, 349, 362, 366, 373; 604/165, 208

[56] References Cited

U.S. PATENT DOCUMENTS

| | | | |
|---|---|---|---|
| 2,847,990 | 8/1958 | Ayre | 600/569 |
| 3,633,422 | 1/1972 | Grieshaber | 73/219 |
| 3,830,225 | 8/1974 | Shinnick | 600/581 |
| 4,227,537 | 10/1980 | Suciu et al. | |
| 4,245,653 | 1/1981 | Weaver | |
| 4,257,427 | 3/1981 | Bucalo | 600/582 |
| 4,824,247 | 4/1989 | True et al. | 356/244 |
| 5,327,908 | 7/1994 | Gerry | 600/587 |
| 5,380,295 | 1/1995 | Vacca | 604/208 |
| 5,749,887 | 5/1998 | Heske et al. | 606/185 |
| 5,823,954 | 10/1998 | Chaffringeon | 600/367 |

FOREIGN PATENT DOCUMENTS

| | | |
|---|---|---|
| 0 283 272 | 9/1988 | European Pat. Off. |
| 0 304 321 | 2/1989 | European Pat. Off. |
| 2 353 640 | 12/1977 | France |
| 2 390 149 | 12/1978 | France |
| U-85 31 432 | 5/1988 | Germany |
| 1319837 | 6/1987 | U.S.S.R. ................................. 600/562 |
| 2208603 | 4/1989 | United Kingdom ..................... 600/569 |
| WO 91016855 | 11/1991 | WIPO ..................................... 600/569 |

OTHER PUBLICATIONS

Ernest Ayre, A New Diagnostic Procedure for Cancer of the Larynx Using a Retractable Throat Brush, from the cancer institute at Miami, Cancer Research and Cytology Center, J.A.M.A., Oct. 23, 1954.

Unibac, The Unibac System from Bio–Dynamics, Inc., Apr. 1979.

*Primary Examiner*—Richard J. Apley
*Assistant Examiner*—Justine R. Yu
*Attorney, Agent, or Firm*—Oliff & Berridge, PLC

[57] ABSTRACT

A portable device for extemporaneous analysis of a body fluid in an intracorporeal cavity includes a tube adapted for introduction into the cavity and a rod slidably mounted in the tube. The rod has a gripping end which emerges from one end of the tube, and a second end that has elements for sampling of body fluid. The rod is capable of assuming two relative positions with respect to the tube, one retracted and the other deployed. The second end of the rod has two branches which can be spaced apart angularly, and the free end of each of the branches has elements for sampling of the body fluid. The branches are arranged in relation with the tube in such a way that, in the retracted position, the sampling elements of the two branches are drawn together and remain at a distal end of the tube, and in the deployed position, the branches are spaced apart outside the distal end of the tube.

5 Claims, 2 Drawing Sheets

PORTABLE DEVICE FOR EXTEMPORANEOUS ANALYSIS OF A BODY-FLUID

BACKGROUND OF THE INVENTION

The present invention relates to the extemporaneous analysis of a body fluid or liquid, which is present in an intracorporeal cavity, by means of a portable, and if appropriate disposable, device. By way of a non-limiting example of the scope of the present invention, the latter relates to the extemporaneous analysis of the cervical mucus which is present in the uterine neck of the vagina of the female body.

The subject of the present invention is a portable, and if appropriate disposable, device which is particularly simple as regards its use and which safeguards the intracorporeal cavity, and especially its mucous membrane, from any contact with analysis reagents.

DESCRIPTION OF THE PRIOR ART

According to the document DE-U-85 31432, a portable device has been proposed and described uniquely for taking samples of intrauterine mucus, and intrauterine fluid, and this by way of the uterine neck.

This device comprises:

- a tube adapted to pass through the uterine neck, so as to take up position temporarily in the intrauterine cavity;
- a rod mounted in the manner of a sealed plunger, so as to slide in the tube, including a gripping end which emerges from one side of said tube, and at the other end an elastic ring capable of assuming two positions, namely an open position in the intrauterine cavity, and a closed or clamped position inside the tube; this elastic ring is itself made up of four continuous branches, symmetrical in pairs with respect to the axis of the tube, namely, in the open position, two branches widening out from the distal end of the tube, and two branches forming an obtuse angle joining them; two symmetrical branches of the sampling means are thus capable of being spaced apart angularly with respect to one another;
- the rod being capable of assuming at least two positions with respect to the tube, namely a retracted position, in which the branches of the sampling means are drawn together in pairs, and in which the abovementioned ring is closed or clamped, and a deployed position in which the branches spread apart in pairs, outside the tube, at its distal end, in order to obtain the open position of the abovementioned ring.

Such a device cannot also be used for a particular analysis or measurement of the biological specimen and/or body fluid sampled, since in particular the sample taken has to be transferred to and analyzed in a laboratory, for example for anatomical and pathological examination.

Moreover, such a device is brought in its deployed position, with the sampling ring completely open, into the intrauterine cavity itself. This results in a medical maneuver which is aggressive, and even traumatizing for the patient.

The subject of the present invention is a device for taking a sample of, more particularly, a body fluid, and not a biological cell specimen (as for a biopsy), and permitting, with the same means, a direct, extemporaneous analysis or measurement of the body fluid sampled, and this without aggression vis-à-vis the patient.

In accordance with the present invention, the sampling means comprises two branches, each one including a free end provided with an element for sampling of the body fluid. These sampling elements are drawn together and protruding at the distal end of the tube, in the retracted position of the rod. They are spaced apart from one another outside the tube, in the deployed position of this same rod. Thus, the sampling device is also adapted for extemporaneous measurement of the spinnbarkeit of the body fluid sampled, between the two sampling elements, in the deployed and spaced-apart position of the two branches, outside the intracorporeal cavity. these two branches are arranged in relation or with respect to the tube in such a way that, in the retracted position of the rod, the sampling elements of the two branches are drawn together and remain at the distal end of the tube, and in a deployed position these same sampling elements are spaced apart outside the tube, at its distal end.

The functioning of such a device is as follows:

- when the rod is in the retracted position with respect to the tube, the device is introduced into the intracorporeal cavity until contact is made between the distal end of the tube and the wall of said cavity, for example the mucous membrane of the cervix;
- by moving the distal end of the device, and the sampling elements protruding from said end, the latter are made to rub against the wall of the intracorporeal cavity, by means of which it is possible to remove body fluid, for example the cervical mucus, and to retain it on said elements;
- the whole of the device is then withdrawn from the intracorporeal cavity;
- outside the intracorporeal cavity, the rod is displaced gradually and slowly with respect to the tube, so as to pass from the retracted position to the deployed position, by which means the body fluid lengthens out, without breaking up, in a sort of continuous filament or thread between the two branches of the rod, and more particularly between the two sampling elements;
- finally, the thread or filament of the body fluid ruptures at a relative position of the rod with respect to the tube which can vary as a function of the spinnbarkeit of the body fluid; observation of the position of the rod with respect to the tube, corresponding to the rupture of the thread or filament of the body fluid, thus constitutes a measure of the spinnbarkeit of the analyzed body fluid.

DESCRIPTION OF THE DRAWINGS

The present invention is now described with reference to the attached drawing, in which.

DESCRIPTION OF THE PREFERRED EMBODIMENTS

Figure 1:
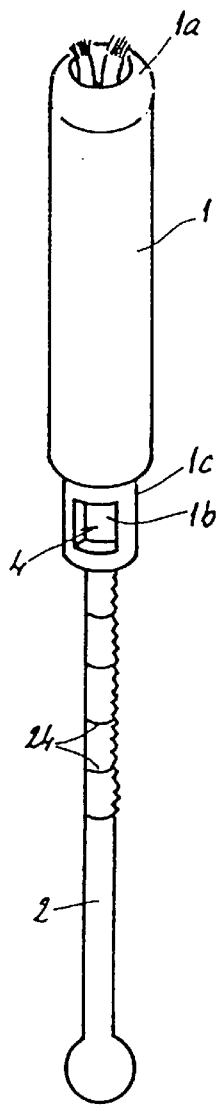
FIG. 1 represents a perspective view of the device according to a first embodiment of the invention, in its retracted position.

A device according to the invention can be made of any suitable material, in particular biocompatible plastic. This device comprises in a general manner a tube 1 generally rounded at its distal end and having a shoulder at its proximal end. This tube is adapted in shape and dimensions for introduction into the intracorporeal cavity, for example the vaginal cavity of the woman.

A rod 2 is mounted slidably in the tube 1 and comprises, at the proximal end 1c of the tube 1, a gripping end 21, and two branches 22 and 23 which emerge from the distal end 1a of the tube 1 and which are capable of being spaced apart angularly, with an inherent elasticity bringing them back to the spaced-apart position. The free end of each branch 22 or 23 comprises an element 3 for sampling of the body fluid, said element 3 being in the form of hairs or filaments. The rod 1 is provided with serrations 2c, at the side opposite the branches 22 and 23, while a catch 16 forms an integral part of the tube 1, inside its bore, and makes it possible to immobilize the rod 1 in a relative position with respect to the tube 2.

The tube 1 can be covered if appropriate with a temporary protective means (not represented) such as a sheath surrounding or at least partially enclosing, and in a sealing manner, the tube 1 and the elements 3 for sampling of the body fluid. Such a sheath can comprise, or can be integral with, one end of an attachment, for example a pulling loop, with which it is possible to withdraw the sheath in order to expose the tube 1, and also the sampling elements 3 of the device, after the tube 1 has been introduced into the intracorporeal cavity.

Figure 2:
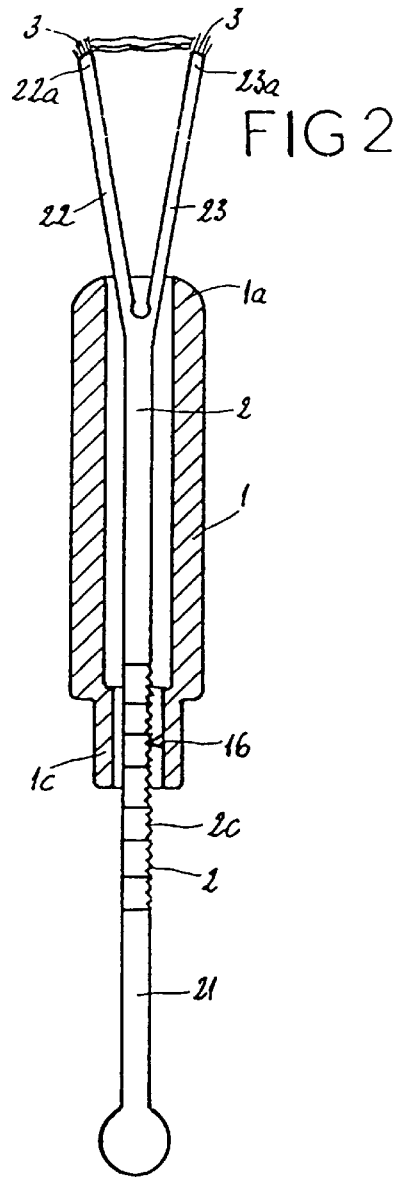
FIG. 2 is a view of the device represented in FIG. 1, in the deployed position.

The rod 2 is capable of assuming two relative positions with respect to the tube 1, the one retracted (i.e., a sampling or protruding position), as shown in FIG. 1, in which the sampling elements 3 of the two branches 22 and 23 respectively are drawn together and emerge at a distal end 1a of the tube 1, and the other deployed (i.e., a measuring position), as represented in FIG. 2, in which the branches 22 and 23 are spaced apart outside the tube 1, at its distal end 1a.

The device according to the invention is equipped with a means 4 for measuring, in particular for reading off, the relative displacement of the rod 2 with respect to the tube 1. This reading-off means 4 comprises markings 24 engraved or present on the rod 2, and a reading window 1b formed on the tube 1, and more specifically at its proximal end 1c.

Figure 3:
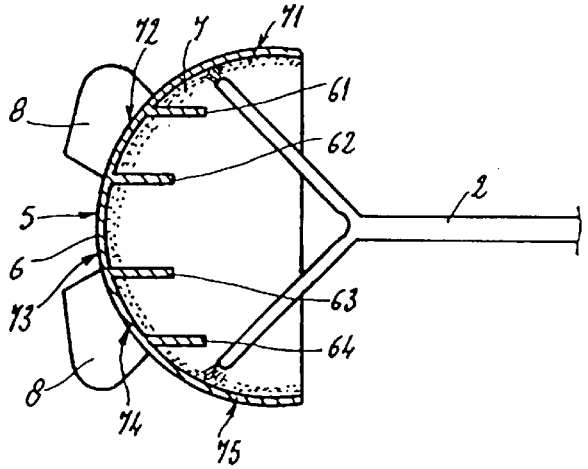
FIG. 3 represents a complementary embodiment of the present invention, consisting of a complementary analysis element.

In accordance with FIG. 3, a complementary analysis element 5 for analyzing a constituent of the body fluid, for example an enzyme present in the cervical mucus, or a chemical, biochemical or biological state, for example the pH of said fluid, is adapted to be brought into contact with the sampling elements 3 of one or both branches 22 and 23 of the rod 2. This complementary analysis element comprises a cup 6, in particular of transparent material, and reaction means 7, for example color oxidation-reduction reagents, distributed or disposed inside the cup 6 and capable of reacting, in a manner visible or perceptible to the user, with at least one constituent of the body fluid, or in the presence of the sought state of said fluid. The shape and the dimensions of this cup are adapted so as to bring the sampling elements 3 into contact with the reaction means 7; for example, as is shown in FIG. 3, the cup has a hollow and spherical shape.

In order to permit the manipulation of the complementary analysis element 5 with respect to the branches 22 and 23 of the rod 2, the cup 6 has external manipulation studs 8.

The inside of the cup 6 has partitions 61 to 64 which delimit different reaction zones 71 to 75, respectively, in which respectively different reagents, in particular color reagents, are disposed.

Figures 4A, 4B:
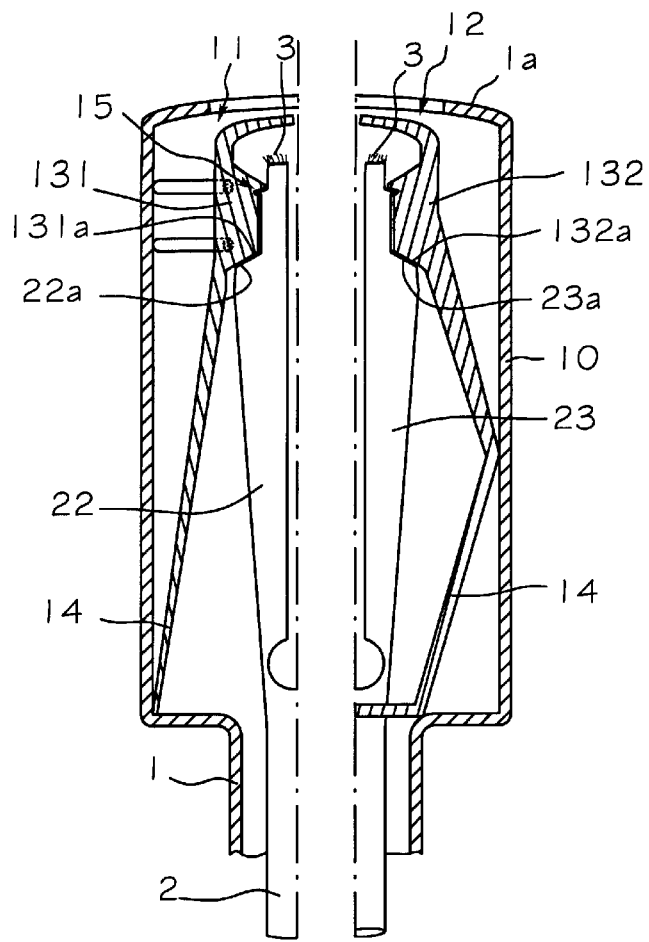
FIG. 4a is a partial sectional view showing the left side of a second embodiment of the invention.
FIG. 4b is a partial sectional view showing the right side of a third embodiment of the invention.

The devices represented in FIGS. 4a and 4b differs from that described with reference to FIGS. 1 and 2 in terms of the following characteristics:

the branches 22 and 23 are arranged in relation with the tube 1 in such a way that, in the retracted position shown in FIGS. 4a and 4b (i.e., a resting or protected position), the sampling elements 3 are disposed side by side and inside the tube 1, which is continued via the head 10 described hereinafter;

the tube 1 comprises a distal part or a head 10 for the accommodation of the two branches 22 and 23 in the position in which they are drawn together and retracted; this head comprises an aperture 11 for the passage of the two branches 22 and 23, in the position in which they are drawn together, as shown in FIGS. 4a and 4b, and a closure member 12 for the aperture 11, closing the latter when the rod 2 is in the retracted position, and freeing this same aperture for the passage of the two branches, which are drawn together, when the rod 2 is displaced toward the outside from the distal end 1a of the tube 1, for example toward its deployed position;

the closure member 12 comprises two flap elements 131 and 132 mounted in a retractable manner in the aperture 11 of the head 10 and held in the closed position in this aperture; these two mutually facing flap elements 131 and 132 are retractable in the opposite direction with respect to one another, and are returned toward one another by the return means 14; in accordance with the representation of FIG. 4b, this return means consists of a blade forming a spring which is integral with the actual flap element 131 or 132, bearing on the wall of the head 10, and fixed in position at its free end by sliding on the rod 2; in accordance with the representation on the left-hand half of FIG. 4, the flap element 131 or 132 is guided in translation, perpendicular to the axis of the tube 1, by suitable bearing grooves cooperating with corresponding studs protruding from said element, and the return means 14, again integral with the flap element, consist of a return blade bearing at its free end against the wall of the tube 1, and more specifically of the head 10;

each flap element 131 or 132 comprises its own means of retraction, under the effect of the displacement of each corresponding branch 22 or 23 toward the outside of the tube via the aperture 11; these retraction means consist of a ramp 131a or 132a cooperating with a corresponding shoulder 22a or 23a present on each corresponding branch 22 or 23;

each flap element 131 or 132 comprises a locking means 15 for locking a corresponding branch 22 or 23 in the retracted position of the rod 2, it being understood that each branch 22 or 23 can escape from said locking means 15 when the rod 2 is displaced toward the outside of the tube 1; this locking means consists of a rib provided on a flap element 131 or 132, in line with a stud protruding laterally from a branch 22 or 23.

Figures 5A, 5B:
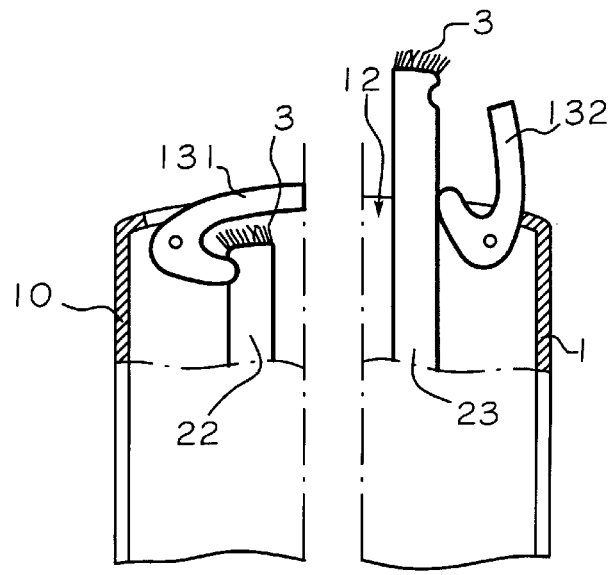
FIGS. 5a and 5b relate to a fourth embodiment of the invention, FIG. 5a showing the left side of the device when the rod and its two branches are in a retracted position, and FIG. 5b showing the right side of the device when the rod and its two branches are in a deployed position.

In accordance with the representations in FIGS. 5a and 5b, each flap element 131 or 132 is articulated on the head 10 and comprises an active end in the form of a hook cooperating with a corresponding groove formed at the upper end of a branch 22 or 23. In this way, in the retracted position shown in FIG. 5a, the flap elements 131 and 132 are blocked in the closed position of the closure member 12, while they escape from the same branches when the latter are displaced toward the outside of the tube 1, as is shown in FIG. 5b (i.e., a sampling or protruding position), this displacement causing their rotation into the open position of the closure member.

The features which have been described with reference to FIGS. 4a, 5a and 5b make it possible at one and the same time to protect the sampling means 3 upon introduction of the device into the intracorporeal cavity, to free them or expose them to the body fluid in this cavity alone, then to bring them back into the retracted position, and thereby to protect them upon withdrawal of the device from the intracorporeal cavity, the deployed and spaced-apart position of the two branches being obtained outside this same cavity.

In summary, an analysis device is obtained, in accordance with the invention, which is particularly simple and effective and which protects the intracorporeal cavity from any contact with reagents.

What is claimed is:

1. A portable device intended for sampling a body fluid in an intracorporeal cavity, comprising a tube adapted for introduction into said cavity, a rod mounted slidably in said tube and having at its proximal end a gripping end which emerges from said tube, and having at its distal end two branches capable of being spaced apart angularly, each branch including a free and distal end provided with an element for sampling of the body fluid, said rod being capable of assuming at least two relative positions with respect to said tube, namely a retracted position in which the two branches are drawn together and said sampling elements protrude at the distal end of the tube, and in which said device is introduced into said intracorporeal cavity, and outside of said intracorporeal cavity a deployed position in which said branches spread apart outside of said tube at its distal end, and in which said device is adapted for extemporaneous measurement between the two sampling elements of the spinnbarkeit of the body fluid sampled in said retracted position in said intracorporeal cavity.

2. The device as claimed in claim 1, wherein the rod defines serrations, and the tube includes a catch, the serrations and the catch being communicable to immobilize the rod at various positions relative to the tube.

3. A method of extemporaneously analyzing a body fluid in an intracorporeal cavity, said method using a device comprising a tube and a rod slidably mounted in said tube and having a gripping end which emerges from one end of said tube, and a second end of the rod having two branches, a free and distal end of each of said branches having sampling elements, said method comprising the successive steps of:

retracting said rod in said tube in a retracted position wherein said two branches are drawn together and said sampling elements protrude at the distal end of the tube;

introducing said device into said intracorporeal cavity, and sampling said body fluid with said sampling elements in the retracted position of said device;

withdrawing said device from said intracorporeal cavity, with said sampled body fluid on said sampling elements;

outside of said intracorporeal cavity, deploying said rod from said tube in a deployed position wherein said two branches are spaced apart outside said tube at said second end of said tube; and in the deployed position of the device, measuring between said two sampling elements the spinnbarkeit of the sampled body fluid.

4. The method as claimed in claim 3, further comprising the step of contacting serrations of the rod with a catch of the tube to immobilize the rod at a certain position relative to the tube.

5. A portable device for extemporaneous analysis of a body fluid in an intracorporeal cavity, comprising:

a tube adapted for introduction into said cavity;

a rod slidably mounted in said tube and having a gripping end which emerges from one end of said tube, and a second end of the rod having two branches, a free and distal end of each of said branches having sampling elements;

means for retracting said rod in said tube in a retracted position wherein said two branches are drawn together and said sampling elements protrude at the distal end of the tube;

means for introducing said device into said intracorporeal cavity, and sampling said body fluid with said sampling elements in the retracted position of said device;

means for withdrawing said device from said intracorporeal cavity, with said sampled body fluid on said sampling elements;

means for deploying said rod from said tube in a deployed position, outside of said intracorporeal cavity, wherein said two branches are spaced apart outside said tube at said second end of said tube; and means for measuring between said two sampling elements, in the deployed position of the device, the spinnbarkeit of the sampled body fluid.

* * * * *